(12) United States Patent
Hastrup et al.

(10) Patent No.: US 6,506,589 B1
(45) Date of Patent: Jan. 14, 2003

(54) USEFUL MUTATIONS OF BACTERIAL ALKALINE PROTEASE

(75) Inventors: Sven Hastrup, København (DK); Sven Branner, Lyngby (DK); Fanny Norris, Hellerup (DK); Steffen Bjørn Petersen, Ballerup (DK); Leif Nørskov-Lauridsen, Køge (DK); Villy Johannes Jensen, Bagsvaerd (DK); Dorrit Aaslyng, Roskilde (DK)

(73) Assignee: Novozymes, A/S, Bagsvaerd (DK)

( * ) Notice: Subject to any disclaimer, the term of this patent is extended or adjusted under 35 U.S.C. 154(b) by 0 days.

(21) Appl. No.: 08/486,846

(22) Filed: Jun. 7, 1995

Related U.S. Application Data

(62) Division of application No. 07/294,241, filed on Jan. 6, 1989, now abandoned.

(30) Foreign Application Priority Data

Jan. 7, 1988 (DK) .............................................. 00064/88

(51) Int. Cl.$^7$ .......................... C12N 9/56; C12N 15/57; C12N 15/74; C12N 3/386; C11D 3/386
(52) U.S. Cl. .................... 435/221; 435/69.1; 435/172.3; 435/220; 435/222; 435/252.3; 435/252.31; 435/320.1; 435/471; 536/23.2; 510/300
(58) Field of Search ................................ 435/219–222, 435/69.1, 172.3, 252.31, 320.1; 536/23.2; 510/300, 320, 374

(56) References Cited

U.S. PATENT DOCUMENTS

| | | | | |
|---|---|---|---|---|
| 3,723,250 A | | 3/1973 | Aunstrup et al. ............ | 435/221 |
| 4,752,585 A | * | 6/1988 | Koths et al. ................ | 435/256 |
| 4,760,025 A | * | 7/1988 | Estell et al. ................ | 510/392 |
| 4,914,031 A | * | 4/1990 | Zukowski et al. .......... | 435/222 |
| 4,980,288 A | * | 12/1990 | Bryan et al. ................ | 435/222 |
| 5,217,878 A | * | 6/1993 | van Eekelen et al. ....... | 345/69.1 |
| 5,665,587 A | * | 9/1997 | Aaslyng et al. ............. | 435/221 |
| 5,700,676 A | * | 12/1997 | Bott et al. .................. | 435/221 |
| 5,741,694 A | * | 4/1998 | Hastrup et al. ............. | 435/221 |
| 5,763,257 A | * | 6/1998 | Bott et al. .................. | 435/221 |
| 5,801,038 A | * | 9/1998 | Bott et al. .................. | 435/221 |
| 6,190,900 B1 | * | 2/2001 | Sierkstra et al. ............ | 435/221 |
| 6,197,567 B1 | * | 3/2001 | Aaslyng et al. ............. | 435/221 |

FOREIGN PATENT DOCUMENTS

| | | | |
|---|---|---|---|
| EP | 0 283 075 | * | 9/1988 |
| WO | WO 87/04461 | * | 7/1987 |

OTHER PUBLICATIONS

Wright, C.S., et al., Nature, vol. 221, "Structure of subtilisin PBN' at 2.5A resolution", pp. 235–241, 1969.*
Stauffer, C.E., et al., The Journal of Biological Chemistry, vol. 344, "The effect on subtilisin activity of oxidizing a methionine residue", pp. 5333–5338, 1969.*
Alden, R. A., et al., Philosophical Transactions of the Royal Society of London, Series B, vol. 257, "A hydrogen–bond network at the active site of subtilisin BPN'", pp. 119–124, 1970.*
Kraut, J., et al., Cold Spring Harbor Symposia on Quantitative Biology, vol. 36, "The aromatic substrate binding site in subtilisin BPN' and its resemblance to chymotrypsin", pp. 117–123, 1971.*
Robertus, J. D., et al., Biochemical and Biophysical Research Communications, vol. 42, "On the identity of subtilisins BPN' Novo", pp. 334–339, 1971.*
Drenth, J., et al., European Journal of Biochemistry, vol. 26, "Subtilisin Novo—The three–dimensional structure and its comparison with subtilisin BPN'", pp. 177–181, 1972.*
Robertus, J. D., et al., Biochemistry, vol. 11, "An X–ray crystallographic study of the binding of peptide chloromethyl ketone inhibitors to subtilisin BPN'", pp. 2439–2449, 1972.*
Robertus, J. D., et al., Biochemistry, vol. 11, "Subtilisin; a stereochemical mechanism involving transition–state stabilization", pp. 4239–4303, 1972.*
Barker, W. C., et al., in Atlas of Protein Sequence and Structure, Dayhoff, M. O., Ed., vol. 5, "Detecting distant relationships: Computer methods and results", pp. 101–110, National Biomedical Research Foundation, Publ., Washington, D.C., 1972.*
Kurihara, M., et al., The Journal of Biological Chemistry, vol. 247, "Subtilisin amylosacchariticus", pp. 5619–5631, 1972.*
Poulos, T. L., et al., The Journal of Biological Chemistry, vol. 251, "Polypeptide halomethyl ketones bind to serine proteases as analogs of the tetrahedral intermediate", pp. 1097–1103, 1976.*
Voordouw, G., et al., Biochemistry, vol. 15, "Role of bound calcium ions in thermostable, proteolytic enzymes. Separation of intrinsic and calcium ion contributions to the kinetic thermal energy.", pp. 3716–3723, 1976.*
Svendsen, Ib, Carlsberg Research Communications, vol. 41, "Chemical modifications of the subtilisins with special reference to the binding of large substrates. A review.", pp. 237–291, 1976.*

(List continued on next page.)

Primary Examiner—Ponnathapu Achutamurthy
Assistant Examiner—William W. Moore
(74) Attorney, Agent, or Firm—Elias J. Lambiris

(57) ABSTRACT

The present invention relates to mutations of the subtilisin gene, some of which result in changes in the chemical characteristics of subtilisin enzyme. Mutations are created at specific nucleic acids of the subtilisin gene and, in various specific embodiments, the mutant enzymes possess altered chemical properties including, but not limited to, increased stability to oxidation, augmented proteolytic activity, and improved washability. The present invention also relates, but is not limited to, the amino acid and DNA sequences for two proteases derived from *Bacillus lentus* variants, subtilisin 147 and subtilisin 309, as well as mutations of these genes and the corresponding mutant enzymes.

9 Claims, 6 Drawing Sheets

OTHER PUBLICATIONS

Wells, J. A., et al., Nucleic Acids Research, vol. 11, "Cloning, sequencing, and secretion of *Bacillus amyloliquefaciens subtilisin* in *Bacillus subtilis*", pp. 7911–7925, 1983.*

Phillipp, M., et al., Molecular and Cellular Biochemistry, vol. 51, "Kinetics of subtilisin and thiolsubtilisin", pp. 5–32, 1983.*

Brot, N., et al., Archives of Biochemistry and Biophysics, vol. 223, "Biochemistry and physiological role of methionine sulfoxide residues in proteins", pp. 271–281, 1983.*

Hirono, S., et al., Journal of Molecular Biology, vol. 178, "Crystal structure at 2.6A resolution of the complex of subtilisin BPN' with *Streptomyces subtilisin* inhibitor", pp. 389–413, 1984.*

Pahler, A., et al., The EMBO Journal, vol. 3, "Three–dimensional structure of fungal proteinase K reveals similarity to bacterial subtilisin", pp. 1311–1314, 1984.*

Einspahr, H., et al., in Metal Ions In Biological Systems, Sigel, H., Ed., "Crystal structure studies of calcium complexes and implications for biological studies", pp. 51–97, Marcel Dekker, Inc., Publ., New York, NY, 1984.*

Estell, D. A., et al., World Biotechnology Report, vol. 2, "Site–directed mutagenesis of the active site of subtilisin BPN'", pp. 181–187, 1984.*

Jany, K.–D., et al., Biological Chemistry Hoppe–Seyler, vol. 366, "Proteinase K from Tritirachium album limber", pp. 485–492, 1985.*

Estell, D. A., et al., The Journal of Biological Chemistry, vol. 260, "Engineering an enzyme by site–directed mutagenesis to be resistant to chemical oxidation", pp. 6518–6521, 1985.*

McPhalen, C. A., et al., FEBS letters, vol. 188, "Crystal and molecular structure of the inhibitor eglin from leeches in complex with subtilisin Carlsberg", pp. 55–58, 1985.*

Thomas, P. G., et al., Nature, vol. 318, "Tailoring the pH dependence of enzyme catalysis using protein engineering", pp. 375–376, 1985.*

Bode, W., et al., The EMBO Journal, vol. 5, "Refined 1.2A crystal structure of the complex formed between subtilisin Carlsberg and the inhibitor elgin c. Molecular structure of eglin and its detailed interaction with subtilisin", pp. 813–818, 1986.*

Wells, J. A., et al., Philosophical Transactions of the Royal Society of London, vol. 317, "Importance of hydrogen–bond formation in stabilizing the transition state of subtilisin", pp. 415–423, 1986.*

Estell, D. A., et al., Science, vol. 233, "Probing steric and hydrophobic effects on enzyme substrate interactions by protein engineering", pp. 659–663, 1986.*

Bryan, P. N., et al., Proteins: Structure, Function, and Genetics, vol. 1, "Proteases of enhanced stability: Characterization of a thermostable variant of subtilisin", pp. 326–334, 1986.*

Bryan, P., et al., Journal of Cellular Biochemistry, Supplement 10, Part A, "Protein engineering of subtilisin: Proteases of enhanced stability", p. 271, Abstract No. E101, 1986.*

Wells, J. A., et al., Journal of Cellular Biochemistry, Supplement 10, Part A, "Subtilisin: A model for protease engineering and secretion," p. 246, Abstract No. E29, 1986.*

Bryan, P., et al., Proceedings of the National Academy of Sciences, U.S.A., vol. 83, "Site–directed mutagenesis and the role of the oxyanion hole in subtilisin", pp. 3743–3745, 1986.*

Pantoliano, M. W., et al., Biochemistry, vol. 26, "Protein engineering of subtilisin BPN': Enhanced stabilization through the introduction of two cysteines to form a disulfide bond", pp. 2077–2082, 1987.*

Mitchinson, C., et al., Journal of Cellular Biochemistry, Supplement 11, Part C, "Engineered disulfide bonds in subtilisin", p. 245, Abstract No. N516, 1987.*

Estell, D. A., et al., Journal of Cellular Biochemistry, Supplement 11, Part C, "Tailoring enzymatic properties through multiple mutations", p. 200, Abstract No. NO24, 1987.*

Wells, N. A., et al., Proceedings of the National Academy of Sciences, U.S.A., vol. 84, "Recruitment of substrate specificty properties from one enzyme into a related one by protein engineering", pp. 5167–5171, 1987.*

Cunningham, B. C., et al., Protein Engineering, vol. 1, "Improvements in the alkaline stability of subtilisin using an efficient random mutagenesis and screening procedure", pp. 319–325, 1987.*

Russell, A. J., et al., Journal of Molecular Biology, vol. 193, "Electrostatic effects on modification of charged groups in the active site cleft of subtilisin by protein engineering", pp. 803–813, 1987.*

Wells, J. A., et al., in Protein Engineering, Oxender, D. L. et al., Eds., "Protein engineering of subtilisin", pp., 279–287, Alan R. Liss, Inc., Publ. New York, NY., 1987.*

Sternberg, M. J. E., et al., Nature, vol. 330, "Prediction of electrostatic effects of engineering of protein charges", pp. 86–88, 1987.*

Bott, R., et al., in Biotechnology in Agricultural Chemistry, LeBaron, H., et al., Eds., "Importance of conformational variability in protein engineering of subtilisin", pp. 139–147, American Chemical Society, Publ., 1987.*

Carter, P., et al., Nature, vol. 332, "Dissecting the catalytic triad of a serine protease", pp. 394–398, 1988.*

Betzel, C., et al., Journal of Molecular Biology, vol. 204, "Crystallization and preliminary X–ray diffraction studies of an alkaline protease from *Bacillus lentus*," pp. 803–804, 1987.*

Wells et al., 1988, TIBS 13:291–197.

Rao et al., 1987, Nature 328:551–554.

Wells et al., 1987, Proc. Natl. Acad. Sci. U.S.A. 84:1219–1223.

Hwang et al., 1987, Biochemistry 26:2669–2673.

Svendsen, et al., 1986, FEBS Lett. 196:228–232.

Jany et al., 1985, Biol. Chem. Hoppe–Seyler 366:485–492.

Meloun et al., 1985, FEBS Lett. 183:195–200.

Nedkov et al., 1985, Biol. Chem. Hoppe–Seyler 366:421–430.

Jacobs et al., 1985, Nucl. Acids Res. 13:8913–8926.

Stahl et al., 1984, J. Bacteriol. 158:411–418.

Vasantha et al., 1984, J. Bacteriol. 159:811–819.

* cited by examiner

USEFUL MUTATIONS OF BACTERIAL ALKALINE PROTEASE

This application is a divisional of U.S. application Ser. No. 07/294,241, filed Jan. 6, 1989 now abandoned, which is incorporated herein by reference.

1. FIELD OF THE INVENTION

The present invention relates to mutations of the subtilisin gene which result in changes in the chemical characteristics of subtilisin enzyme. Mutations at specific nucleic acids of the subtilisin gene result in amino acid substitutions and consequently, altered enzyme function. Some of these mutant enzymes exhibit physical properties advantageous to industrial applications, particularly in the detergent industry, providing subtilisin which is more stable to oxidation, possesses greater protease activity, and exhibits improved washability.

2. BACKGROUND OF THE INVENTION

2.1. BACILLUS PROTEASES

Enzymes cleaving the amide linkages in protein substrates are classified as proteases, or (interchangeably) peptidases (See Walsh, 1979, Enzymatic Reaction Mechanisms. W.H. Freeman and Company, San Francisco, Chapter 3). Bacteria of the Bacillus species secrete two extracellular species of protease, a neutral, or metalloprotease, and an alkaline protease which is functionally a serine endopeptidase, referred to as subtilisin. Secretion of these proteases has been linked to the bacterial growth cycle, with greatest expression of protease during the stationary phase, when sporulation also occurs. Joliffe et al. (1980, J. Bacterial 141:1199–1208) has suggested that Bacillus proteases function in cell wall turnover.

2.2. SUBTILISIN

A serine protease is an enzyme which catalyzes the hydrolysis of peptide bonds, in which there is an essential serine residue at the active site (White, Handler, and Smith, 1973 "Principles of Biochemistry," Fifth Edition, McGraw-Hill Book Company, New York, pp. 271–272).

The serine proteases have molecular weights in the 25,000 to 30,000 range. They are inhibited by diisopropyl-fluorophosphate, but in contrast to metalloproteases, are resistant to ethylenediamine-tetra acetic acid (EDTA) (although they are stabilized at high temperatures by calcium ion). They hydrolyze simple terminal esters and are similar in activity to eukaryotic chymotrypsin, also a serine protease. The alternative term, alkaline protease, reflects the high pH optimum of the serine proteases, from pH 9.0 to 11.0 (for review, see Priest, 1977, Bacteriological Rev. 41:711–753).

A subtilisin is a serine protease produced by Gram-positive bacteria or fungi. A wide variety of subtilisins have been identified, and the amino acid sequences of at least eight subtilisins have been determined. These include six subtilisins from Bacillus strains, namely, subtilisin 168, subtilisin BPN', subtilisin Carlsberg, subtilisin DY, subtilisin amylosacchariticus, and mesentericopeptidase (Kurihara et al., 1972, J. Biol. Chem. 247:5629–5631; Stahl and Ferrari, 1984, J. Bacteriol. 158: 411–418; Vasantha et al., 1984, J. Bacteriol. 159:811–819, Jacobs et al., 1985, Nucl. Acids Res. 13:8913–8926; Nedkov et al., 1985, Biol. Chem. Hoppe-Seyler 366:421–430; Svendsen et al., 1986, FEBS Lett 196:228–232), and two fungal subtilisins, subtilisin thermitase from *Thermoactinymyces vulgaris* (Meloun et al., 1985, FEBS. Lett. 183:195–200) and proteinase K from *Tritirachium album* (Jany and Mayer, 1985, Biol. Chem. Hoppe-Seyler 366:584–492).

Subtilisins are well-characterized physically and chemically. In addition to knowledge of the primary structure (amino acid sequence) of these enzymes, over 50 high resolution X-ray structures of subtilisin have been determined which delineate the binding of substrate, transition state, products, three different protease inhibitors, and define the structural consequences for natural variation (Kraut, 1977, Ann. Rev. Biochem. 46:331–358). Random and site-directed mutations of the subtilisin gene have both arisen from knowledge of the physical and chemical properties of the enzyme and contributed information relating to subtilisin's catalytic activity, substrate specificity, tertiary structure, etc. (Wells et al., 1987, Proc. Natl. Acad. Sci. U.S.A. 84; 1219–1223; Wells et al., 1986, Phil. Trans. R. Soc. Lond. A. 317:415–423; Hwang and Warshel, 1987, Biochem. 26:2669–2673; Rao et al., 1987, Nature 328:551–554).

2.3. INDUSTRIAL APPLICATIONS OF SUBTILISINS

Subtilisins have found much utility in industry, particularly detergent formulations, as they are useful for removing proteinaceous stains. To be effective, however, these enzymes must not only possess activity under washing conditions, but must also be compatible with other detergent components during storage. For example, subtilisin may be used in combination with amylases, which are active against starches; cellulases which will digest cellulosic materials; lipases, which are active against fats; peptidases, which are active on peptides, and ureases, which are effective against urine stains. Not only must the formulation protect other enzymes from digestion by subtilisin, but subtilisin must be stable with respect to the oxidizing power, calcium binding properties, detergency and high pH of nonenzymatic detergent components. The ability of the enzyme to remain stable in their presence is often referred to as its washing ability or washability.

3. SUMMARY OF THE INVENTION

The present invention relates to mutations of the subtilisin gene, some of which result in changes in the chemical characteristics of subtilisin enzyme. Mutations are created at specific nucleic acids of the subtilisin gene, and, in various specific embodiments, the mutant enzymes possess altered chemical properties including, but not limited to, increased stability to oxidation, augmented proteolytic ability, and improved washability.

The present invention also relates, but is not limited to the amino acid and DNA sequences for two proteases derived from *Bacillus lentus* variants, subtilisin 147 and subtilisin 309, as well as mutations of these genes and the corresponding mutant enzymes.

Site-directed mutation can efficiently produce mutant subtilisin enzymes which can be tailored to suit a multitude of industrial applications particularly in the areas of detergent and food technology. The present invention relates, in part, but is not limited to, mutants of the subtilisin 309 gene which exhibit improved stability to oxidation, augmented protease activity, and/or improved washability.

3.1. ABBREVIATIONS

A=Ala=Alanine
V=Val=Valine

L=Leu=Leucine
I=Ile=Isoleucine
P=Pro=Proline
F=Phe=Phenylalanine
W=Trp=Tryptophan
M=Met=Methionine
G=Gly=Glycine
S=Ser=Serine
T=Thr=Threonine
C=Cys=Cysteine
Y=Tyr=Tryosine
N=Asn=Asparagine
Q=Gln=Glutamine
D=Asp=Aspartic Acid
E=Glu=Glutamic Acid
K=Lys=Lysine
R=Arg=Arginine
H=His=Histidine

4. DESCRIPTION OF THE FIGURES

FIG. 1 illustrates the insertion of a subset of fragments, ranging from 1.5 kb to 6.5 kb in length, generated by partial digestion of Bacillus lentus strain 309 DNA with Sau 3A restriction endonuclease, into Bam HI cut plasmid pSx50. The two resulting plasmids, pSx86 and pSx88, containing the subtilisin 309 gene in opposite orientations, are also shown.

FIG. 2 illustrates the insertion of Bacillus lentus strain 147 DNA fragments into plasmid pSX56. Partial digestion of strain 147 DNA was performed using Sau 3A restriction endonuclease. Fragments ranging in size from 1.5 to 6.5 kb were then ligated into Bam HI cleaved plasmid pSX56. The product, pSX94, contains the subtilisin 147 gene.

FIG. 3 illustrates gapped duplex mutagenesis, using the method of Morinaga et al., (1984, Biotechnology 2: 636–639). It features two plasmids, pSX93 and pSX119, both derived from puC13. pSX93 contains an XbaI-HindIII fragment of the subtilisin 309 gene, and pSX119 contains the remainder of the subtilisin 309 gene in an EcoRI-XbaI fragment. In (A), plasmid pSX93 is cleaved with XbaI and ClaI, and the gapped molecules are mixed with pSX93 cut with ScaI, denatured, and allowed to reanneal so as to generate plasmids with a region of single-stranded DNA extending within the subtilisin 309 coding sequence. A synthetic oligonucleotide, homologous to the subtilisin 309 gene but containing a mutation, is allowed to anneal to the single stranded gap, which is then filled in using the Klenow fragment of DNA polymerase I and T4 DNA ligase. Upon replication of the plasmid, double-stranded mutants of the subtilisin 309 gene are generated. The same procedure is performed in (B), using plasmid pSX119 and EcoRI and XbaI enzymes, to create mutations in the corresponding region of the subtilisin 309 gene.

5. DETAILED DESCRIPTION OF THE INVENTION

Figure 1:
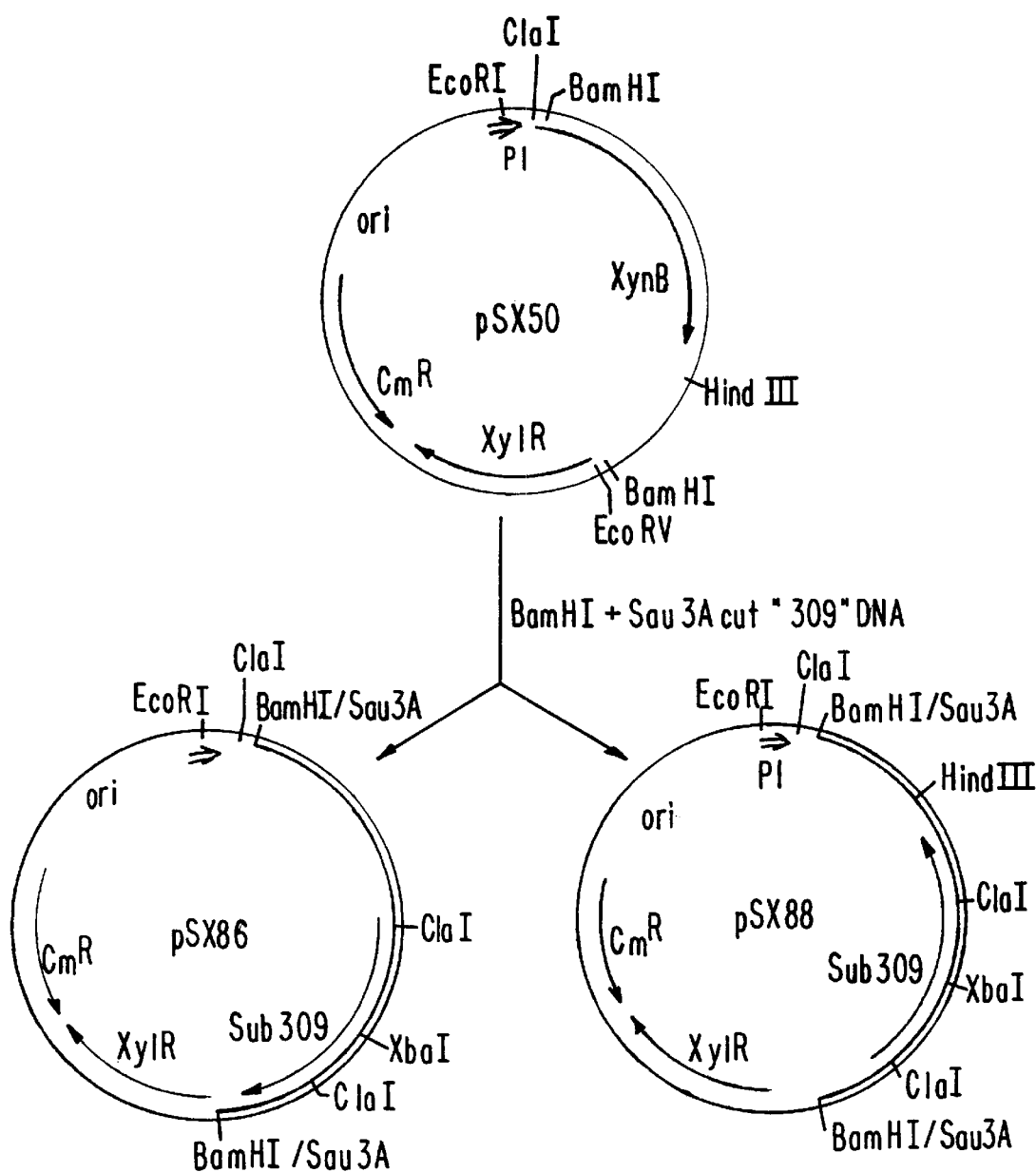

The invention relates to mutations of the subtilisin gene, some of which result in changes in the chemical characteristics of subtilisin enzyme. Mutations at specific nucleic acids may be generated, and thus, forms of subtilisin can be designed so as to meet the needs of industrial application.

The invention is based, in part, upon the discovery that mutations of specific nucleic acids in the subtilisin gene can result in enzymes with altered properties. In various embodiments, enzymes with improved stability to oxidation, augmented protease activity, or improved washing ability can be generated.

For purposes of clarity in description, and not by way of limitation, the invention will be described in four parts: (a) the chemical structure of known subtilisins and subtilisin 147 and 309; (b) methods for producing mutations in the subtilisin gene; (c) expression of mutants of subtilisin and (d) screening of subtilisin mutants for desirable chemical properties.

5.1. Chemical Structures of Known Subtilisins and Subtilisin 147 and 309

Sequence analysis of subtilisin from various sources can reveal the functional significance of the primary amino acid sequence, and can direct the creation of new mutants with deliberately modified functions. Comparing the amino acid sequence of different forms of subtilisin, while contrasting their physical, or chemical properties, may reveal specific target regions which are likely to produce useful mutant enzymes.

The amino acid sequences of at least eight subtilisins are known. These include six subtilisins from Bacillus strains, namely, subtilisin 168, subtilisin BPN', subtilisin Carlsberg, subtilisin DY, subtilisin amylosaccharSSiticus and mesenticopeptidase (Kurihara et al., 1972, J. Biol. Chem. 247:5629–5631; Stahl and Ferrari, 1984, J. Bacteriol. 158:411–418; Vasantha et al., 1984, J. Bacteriol. 159:811–819; Jacobs et al., 1985, Nucl. Acids Res. 13:8913–8926; Nedkov et al., 1985, Biol. Chem. Hoppe-Seyler 366:421–430; Svendsen et al., 1986, FEBS Lett. 196:228–232), and two fungal subtilisins, subtilisin thermitase from Thermoactinymyces vulgaris (Meloun et al., 1985, FEBS Lett. 183:195–200), and proteinase K from Tritirachium album limber (Jany and Mayer, 1985, Biol. Chem. Hoppe-Seyler 366:485–492).

In connection with this invention the amino acid and DNA sequences for two further serine proteases are revealed. These proteases were derived from two Bacillus lentus variants, 147 and 309, which have been deposited with NCIB and designated the accession Nos. NCIB 10147 and NCIB 10309, respectively. For convenience the proteases produced by these strains are designated subtilisin 147 and subtilisin 309, respectively, and the genes encoding these proteins are referred to as the subtilisin 147 and 309 genes.

As used in this invention the term "subtilisin material" refers to a proteinaceous material which contains a subtilisin as its active ingredient. As used herein, and under the definition of subtilisin material, any serine protease is a subtilisin which has at least 30%, preferably 50%, and more preferably 80% amino acid sequence homology with the sequences referenced above for subtilisin 147, subtilisin 309, subtilisin 168, subtilisin BPN', subtilisin Carlsberg, subtilisin DY, subtilisin amylosaccharSSiticus, mesenticopeptidase, thermitase, proteinase K and thermomycolase. These serine proteases are also described herein as "homologous serine proteases".

Table I compares the deduced amino acid sequences of subtilisin 309, subtilisin 147, subtilisin BPN', subtilisin Carlsberg and subtilisin 168 (Spizizen, et al., 1958, Proc.

Natl. Acad. Sci. U.S.A. 44:1072–1078). Table II presents the nucleic acid sequence of the subtilisin 309 gene, and Table III presents the nucleic acid sequence of the subtilisin 147 gene. The sequences of subtilisin 309 or 147, or their functional equivalents, can be used in accordance with the invention. For example, the sequences of subtilisin 309 or 147 depicted in Tables I, II or III can be altered by substitutions, additions or deletions that provide for functionally equivalent molecules. For example, due to the degeneracy of nucleotide coding sequences, other DNA sequences which encode substantially the same amino acid sequence as depicted in Table I may be used in the practice of the present invention. These include but are not limited to nucleotide sequences comprising all or portions of the subtilisin 309 or 147 sequences depicted in Tables II or III which are altered by the substitution of different codons that encode the same or a functionally equivalent amino acid residues within the sequence, thus producing a silent change. For example, one or more amino acid residues within the sequence can be substituted by another amino acid of a similar polarity which acts as a functional equivalent. Substitutes for an amino acid within the sequence may be selected from other members of the class to which the amino acid belongs. For example, the non-polar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine, and histidine. The negatively charged (acidic) amino acids include aspartic and glutamic acid.

Closeness of relation can be measured by comparison of amino-acid sequences. There are many methods of aligning protein sequences, but the differences are only manifest when the degree of relatedness is quite small. The methods described in Atlas of Protein Sequence and Structure, Margaret O. Dayhoff editor, vol. 5, supplement 2, 1976, National Biomedical Research Foundation, Georgetown University Medical Center, Washington, D.C., p. 3 ff., entitled SEARCH and ALIGN, define relatedness. As is well known in the art, related proteins can differ in number of amino acids as well as identity of each amino acid along the chain. That is, there can be deletions or insertions when two structures are aligned for maximum identity. For example, subtilisin Carlsberg has only 274 amino acids while subtilisin BPN' has 275 amino acids. Aligning the two sequences shows that Carlsberg has no residue corresponding to Asn56 of subtilisin BPN'. Thus the amino acid sequence of Carlsberg would appear very different from BPN' unless a gap is recorded at location 56. Therefore, one can predict with a high degree of confidence that substituting Ser for Asn at location 218 of subtilisin Carlsberg will increase thermal stability provided that the residues in Carlsberg are numbered by homology to BPN'.

According to the invention, the sequences determined for subtilisins 309 and 147 can be compared with sequences of known subtilisins (see Table I) or newly discovered subtilisins in order to deduce sites for desirable mutations. To do this, the closeness of relation of the subtilisins being compared must be determined.

Experiments to determine the relationship between the primary structure of subtilisin and its physical properties have revealed the significance of the methionine-222 residue as well as the amino acids functional in the active site, namely, aspartic acid-32, histidine-64, and serine-221. Asparagine-155 and Serine-221 are within the oxyanion binding site. Mutations at these positions are likely to diminish proteolytic activity. According to the present invention, the amino acid sequences of subtilisins 309 and 147 were compared with one another and with the sequences of other subtilisins (see Table II). Residues that varied between subtilisin 309 or 147 and other subtilisins were identified. For example, at residue 153, subtilisin 309 contains a serine residue, whereas subtilisin 147, BPN', Carlsberg and 168 contain an alanine residue. Therefore, if the serine 153 residue of subtilisin 309 were changed to an alanine residue, the physical properties of subtilisin 309 might be altered in a desired direction. Likewise, subtilisin 147 contains a serine residue at position 218, whereas the other subtilisins expressed an asparagine residue. Because subtilisin 147 has improved thermal stability relative to the other subtilisins, mutating the asparagine 218 of subtilisin 309 to a serine residue might improve the thermal stability of subtilisin 309. As another example, it was reasoned that, since Thr 71 is close to the active site, the introduction of a negatively charged amino acid, such as aspartic acid, might suppress oxidative attack by electrostatic repulsion. The sites that are most likely to be relevant to the physical properties of subtilisin are those in which there is conservation of amino residues between most subtilisins, for example Asp-153 and Asn-218 discussed above, and also Trp-6, Arg-170, Pro-168, His-67, Met-175, Gly-219, Arg-275. By mutating the nucleic acid sequence such that a amino acid which differs from other subtilisins is substituted with an amino acid that conforms, a more stable form of subtilisin may result.

Wells et al. (1987, Proc. Natl. Acad. Sci. U.S.A. 84:1219–1223) have used comparison of amino acid sequences and site-directed mutation to engineer subtilisin substrate specificity. The catalytic activities of various subtilisins can differ markedly against selected substrates. Wells has shown that only three amino acid substitutions can cause *B. amyloliquefaciens* subtilisin substrate specificity to approach that of *B. lichenformis* subtilisin, enzymes that differ by factors of 10–50 in catalytic efficiency in their native state. Comparison analysis between subtilisin 147 and 309 and other subtilisins has indicated that mutation of the following sites may alter the physical or chemical properties of subtilisin: 6, 9, 11–12, 19, 25, 36–38, 53–59, 67, 71, 89, 104, 111, 115, 120, 121–122, 124, 128, 131, 140, 153–166, 168, 169–170, 172, 175, 180, 182, 186, 187, 191, 194, 195, 199, 218, 219, 222, 226, 234–238, 241, 260–262, 265, 268, or 275. Deletions occur at the following sites in subtilisins 147 and/or 309; insertion of appropriate amino acid residues into these sights might enhance the stability of the parent enzymes: 1, 36, 56, 159, 164–166. According to the method illustrated by these examples, which are not limiting, a number of potential mutation sites become apparent.

TABLE I

COMPARISON OF AMINO ACID SEQUENCE FOR VARIOUS PROTEASES

```
                        10                      20                      30
a) A-Q-S-V-P-W-G-I-S-R-V-Q-A-P-A-A-H-N-R-G-L-T-G-S-G-V-K-V-A-V-
b) o-Q-T-V-P-W-G-I-S-F-I-N-T-Q-Q-A-H-N-R-G-I-F-G-N-G-A-R-V-A-V-
c) A-Q-S-V-P-Y-G-V-S-Q-I-K-A-P-A-L-H-S-Q-G-Y-T-G-S-N-V-K-V-A-V-
d) A-Q-T-V-P-Y-G-I-P-L-I-K-A-D-K-V-Q-A-Q-G-F-K-G-A-N-V-K-V-A-V-
e) A-Q-S-V-P-Y-G-I-S-Q-I-K-A-P-A-L-H-S-Q-G-Y-T-G-S-N-V-K-V-A-V-

40                      50                      60
a) L-D-T-G-I-°-S-T-H-P-D-L-N-I-R-G-G-A-S-F-V-P-G-E-P-°-S-T-Q-D-
b) L-D-T-G-I-°-A-T-H-P-D-L-R-I-A-G-G-A-S-F-I-S-S-E-P-°-S-Y-H-D-
c) I-D-S-G-I-D-S-S-H-P-D-L-K-V-A-G-G-A-S-M-V-P-S-E-T-N-P-F-Q-D-
d) L-D-T-G-I-Q-A-S-H-P-D-L-N-V-V-G-G-A-S-F-V-A-G-E-A-°-Y-N-T-D-
e) L-D-S-G-I-D-S-S-H-P-D-L-N-V-R-G-G-A-S-F-V-A-S-E-T-N-P-Y-Q-D-

70                      80                      90
a) G-N-G-H-G-T-H-V-A-G-T-I-A-A-L-N-N-S-I-G-V-L-G-V-A-P-S-A-E-L-
b) N-N-G-H-G-T-H-V-A-G-T-I-A-A-L-N-N-S-I-G-V-L-G-V-A-P-S-A-D-L-
c) N-N-S-H-G-T-H-V-A-G-T-V-A-A-L-N-N-S-I-G-V-L-G-V-A-P-S-A-S-L-
d) G-N-G-H-G-T-H-V-A-G-T-V-A-A-L-D-N-T-T-G-V-L-G-V-A-P-S-V-S-L-
e) G-S-S-H-G-T-H-V-A-G-T-I-A-A-L-N-N-S-I-G-V-L-G-V-S-P-S-A-S-L-

100                     110                     120
a) Y-A-V-K-V-L-G-A-S-G-S-G-S-V-S-S-I-A-Q-G-L-E-W-A-G-N-N-G-M-H-
b) Y-A-V-K-V-L-D-R-N-G-S-G-S-L-A-S-V-A-Q-G-I-E-W-A-I-N-N-N-M-H-
c) Y-A-V-K-V-L-G-A-D-G-S-G-Q-Y-S-W-I-I-N-G-I-E-W-A-I-A-N-N-M-D-
d) Y-A-V-K-V-L-N-S-S-G-S-G-T-Y-S-G-I-V-S-G-I-E-W-A-T-T-N-G-M-D-
e) Y-A-V-K-V-L-D-S-T-G-S-G-Q-Y-S-W-I-I-N-G-I-E-W-A-I-S-N-N-M-D-

130                     140                     150
a) V-A-N-L-S-L-G-S-P-S-P-S-A-T-L-E-Q-A-V-N-S-A-T-S-R-G-V-L-V-V-
b) I-I-N-M-S-L-G-S-T-S-G-S-S-T-L-E-Q-A-V-N-R-A-N-N-A-G-I-L-L-V-
c) V-I-N-M-S-L-G-G-P-S-P-S-A-A-L-K-A-A-V-D-K-A-V-A-S-G-V-V-V-V-
d) V-I-N-M-S-L-G-G-P-S-G-S-T-A-M-K-Q-A-V-D-N-A-Y-A-R-G-V-V-V-V-
e) V-I-N-M-S-L-G-G-P-T-G-S-A-A-L-K-T-V-V-D-K-A-V-S-S-G-I-L-V-A-

160                     170                     180
a) A-A-S-G-N-S-G-A-°-G-S-I-S-°-°-°-Y-P-A-R-Y-A-N-A-M-A-V-G-A-T-
b) G-A-A-G-N-T-G-R-°-Q-G-V-N-°-°-°-T-P-A-R-Y-S-G-V-M-A-V-A-A-V-
c) A-A-A-G-N-E-G-T-S-G-S-S-S-T-V-G-Y-P-G-K-Y-P-S-V-I-A-V-G-A-V-
d) A-A-A-G-N-S-G-S-S-G-N-T-N-I-G-Y-P-A-K-Y-D-S-T-V-I-A-V-G-A-V-
e) A-A-A-G-N-E-G-S-S-G-S-S-S-T-V-G-Y-P-A-K-Y-P-S-T-I-A-V-G-A-V-

190                     200                     210
a) D-Q-N-N-N-R-A-S-F-S-Q-Y-G-A-G-L-D-I-V-A-P-G-V-N-V-Q-S-T-Y-P-
b) D-Q-N-G-Q-P-P-S-F-S-T-Y-G-P-E-I-E-I-S-A-P-G-V-N-V-N-S-T-Y-T-
c) D-S-S-S-N-Q-R-A-S-F-S-S-V-G-A-E-L-D-V-M-A-P-G-V-S-I-Q-S-T-L-P-
d) D-S-N-S-N-R-A-S-F-S-S-V-G-A-E-L-E-V-M-A-P-G-A-G-V-Y-S-T-Y-P-
e) N-S-S-N-Q-R-A-S-F-S-S-A-G-S-E-L-D-V-M-A-P-G-V-S-I-Q-S-T-L-P-

220                     230                     240
a) G-S-T-Y-A-S-L-N-G-T-S-M-A-T-P-H-V-A-G-A-A-A-L-V-K-Q-K-N-P-S-
b) G-N-R-Y-V-S-L-S-G-T-S-M-A-T-P-H-V-A-G-V-A-A-L-V-K-S-R-Y-P-S-
c) G-N-K-Y-G-A-Y-N-G-T-S-M-A-S-P-H-V-A-G-A-A-A-L-I-L-S-K-H-P-N-
d) T-S-T-Y-A-T-L-N-G-T-S-M-A-S-P-H-V-A-G-A-A-A-L-I-L-S-K-H-P-N-
e) G-G-T-Y-G-A-Y-N-G-T-S-M-A-T-P-H-V-A-G-A-A-A-L-I-L-S-K-H-P-T-

250                     260                     270
a) W-S-N-V-Q-I-R-N-H-L-K-N-T-A-T-S-L-G-S-T-N-L-Y-G-S-G-L-V-N-A-
b) Y-T-N-N-Q-I-R-Q-R-I-N-Q-T-A-T-Y-L-G-S-P-S-L-Y-G-N-Q-V-H-A-
c) W-T-N-T-Q-V-R-S-S-L-E-N-T-T-T-K-L-G-D-S-F-Y-Y-G-K-G-L-I-N-V-
d) L-S-A-S-Q-V-R-N-R-L-S-S-T-A-T-Y-L-G-S-S-F-Y-Y-G-K-G-L-I-N-V-
e) W-T-N-A-Q-V-R-D-R-L-E-S-T-A-T-Y-L-G-N-S-F-Y-Y-G-K-G-L-I-N-V- a) E-A-A-T-R
b) G-R-A-T-Q
c) Q-A-A-A-Q
d) E-A-A-A-Q
e) Q-A-A-A-Q
``` a = subtilisin 309
b = subtilisin 147
c = subtilisin BPN'
d = subtilisin Carlsberg
e = subtilisin 168
° = assigned deletion

5.2. Methods for Producing Mutations in Subtilisin Genes

Many methods for introducing mutations into genes are well known in the art. After a brief discussion of cloning subtilisin genes, methods for generating mutations in both random sites, and specific sites, within the subtilisin gene will be discussed.

5.2.1. Cloning a Subtilisin Gene

The gene encoding subtilisin may be cloned from any Gram-positive bacteria or fungus by various methods, well known in the art. First a genomic, and/or cDNA library of DNA must be constructed using chromosomal DNA or messenger RNA from the organism that produces the subtilisin to be studied. Then, if the amino-acid sequence of the subtilisin is known, homologous, labelled oligonucleotide probes may be synthesized and used to identify subtilisin-encoding clones from a genomic library of bacterial DNA, or from a fungal cDNA library. Alternatively, a labelled oligonucleotide probe containing sequences homologous to subtilisin from another strain of bacteria or fungus could be used as a probe to identify subtilisin-encoding clones, using hybridization and washing conditions of lower stringency.

Yet another method for identifying subtilisin-producing clones would involve inserting fragments of genomic DNA into an expression vector, such as a plasmid, transforming protease-negative bacteria with the resulting genomic DNA library, and then plating the transformed bacteria onto agar containing a substrate for subtilisin, such as skim milk. Those bacteria containing subtilisin-bearing plasmid will produce colonies surrounded by a halo of clear agar, due to digestion of the skim milk by excreted subtilisin.

5.2.2. Generation of Random Mutations in the Subtilisin Gene

Once the subtilisin gene has been cloned into a suitable vector, such as a plasmid, several methods can be used to introduce random mutations into the gene.

One method would be to incorporate the cloned subtilisin gene, as part of a retrievable vector, into a mutator strain of *Eschericia coli*.

Another method would involve generating a single stranded form of the subtilisin gene, and then annealing the fragment of DNA containing the subtilisin gene with another DNA fragment such that a portion of the subtilisin gene remained single stranded. This discrete, single stranded region could then be exposed to any of a number of mutagenizing agents, including, but not limited to, sodium bisulfite, hydroxylamine, nitrous acid, formic acid, or hydralazine. A specific example of this method for generating random mutations is described by Shortle and Nathans (1978, Proc. Natl. Acad. Sci. U.S.A., 75:2170–2174). According to the Shortle and Nathans method, the plasmid bearing the subtilisin gene would be nicked by a restriction enzyme that cleaves within the gene. This nick would be widened into a gap using the exonuclease action of DNA polymerase I. The resulting single-stranded gap could then be mutagenized using any one of the above mentioned mutagenizing agents.

Alternatively, the subtilisin gene from a Bacillus species including the natural promoter and other control sequences could be cloned into a plasmid vector containing replicons for both *E. coli* and *B. subtilis*, a selectable phenotypic marker and the M13 origin of replication for production of single-stranded plasmid DNA upon superinfection with helper phage IR1. Single-stranded plasmid DNA containing the cloned subtilisin gene is isolated and annealed with a DNA fragment containing vector sequences but not the coding region of subtilisin, resulting in a gapped duplex molecule. Mutations are introduced into the subtilisin gene either with sodium bisulfite, nitrous acid or formic acid or by replication in a mutator strain of *E. coli* as described above. Since sodium bisulfite reacts exclusively with cytosine in a single-stranded DNA, the mutations created with this mutagen are restricted only to the coding regions. Reaction time and bisulfite concentration are varied in different experiments such that from one to five mutations are created per subtilisin gene on average. Incubation of 10 $\mu$g of gapped duplex DNA in 4 M Na-bisulfite, pH. 6.0, for 9 minutes at 37° C. in a reaction volume of 400 $\mu$l, deaminates about 1% of cytosines in the single-stranded region. The coding region of mature subtilisin contains about 200 cytosines, depending on the DNA strand. Advantageously, the reaction time is varied from about 4 minutes (to produce a mutation frequency of about one in 200) to about 20 minutes (about 5 in 200).

After mutagenesis the gapped molecules are treated in vitro with DNA polymerase I (Klenow fragment) to make fully double-stranded molecules and to fix the mutations. Competent *E. coli* are then transformed with the mutagenized DNA to produce an amplified library of mutant subtilisins. Amplified mutant libraries can also be made by growing the plasmid DNA in a Mut D strain of *E. coli* which increases the range of mutations due to its error prone DNA polymerase.

The mutagens nitrous acid and formic acid may also be used to produce mutant libraries. Because these chemicals are not as specific for single-stranded DNA as sodium bisulfite, the mutagenesis reactions are performed according to the following procedure. The coding portion of the subtilisin gene is cloned in M13 phage by standard methods and single stranded phage DNA prepared. The single-stranded DNA is then reacted with 1 M nitrous acid pH. 4.3 for 15–60 minutes at 23° C. or 2.4 M formic acid for 1–5 minutes at 23° C. These ranges of reaction times produce a mutation frequency of from 1 in 1000 to 5 in 1000. After mutagenesis, a universal primer is annealed to the M13 DNA and duplex DNA is synthesized using the mutagenized single-stranded DNA as a template so that the coding portion of the subtilisin gene becomes fully double-stranded. At this point the coding region can be cut out of the M13 vector with restriction enzymes and ligated into an unmutagenized expression vector so that mutations occur only in the restriction fragment. (Myers et al., Science 229:242–257 (1985)).

Figure 5:
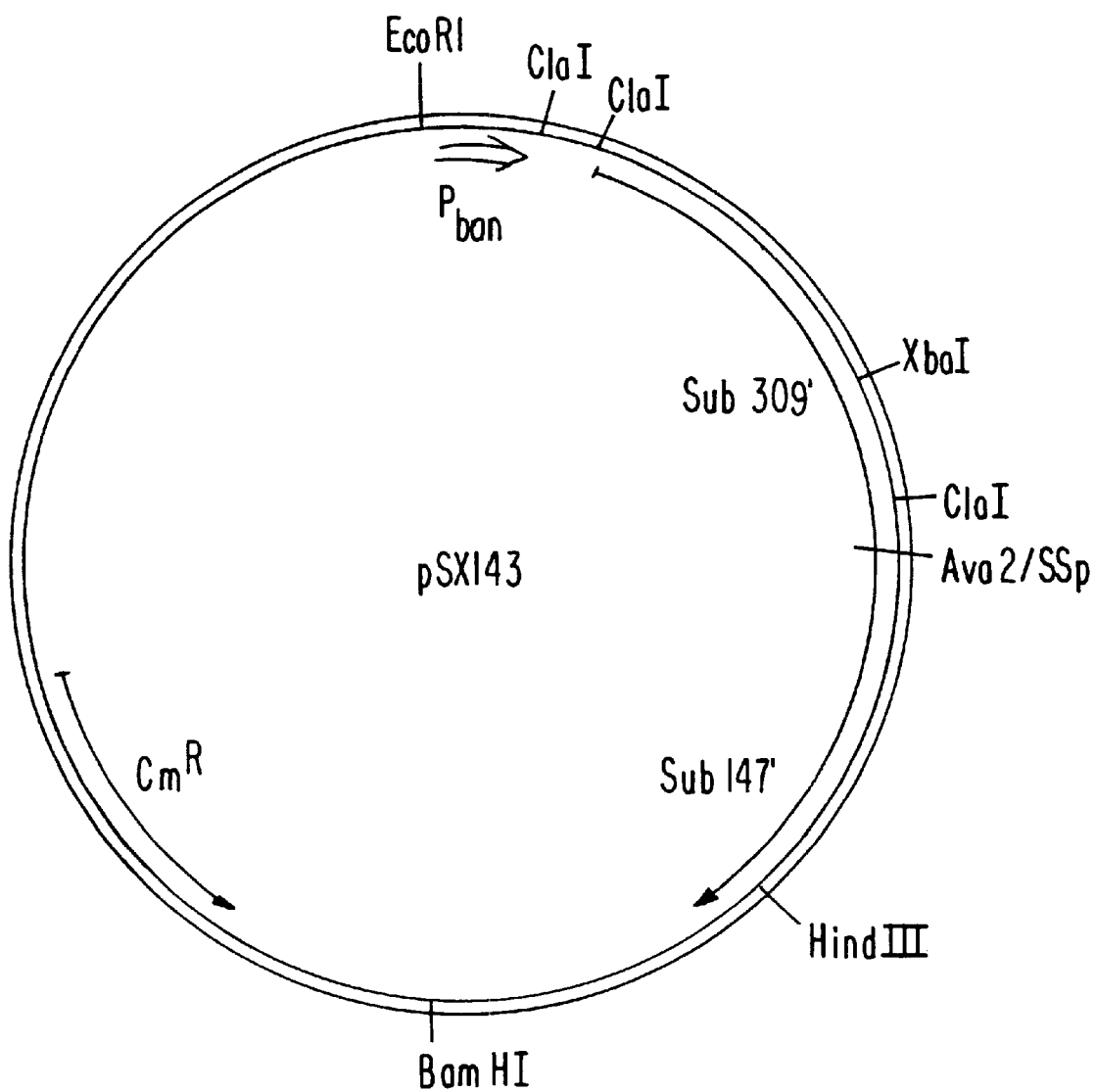
FIG. 5 illustrates plasmid pSX143, which contains truncated forms of both subtilisin 309 and subtilisin 147 genes. In vivo recombination between homologous regions of the two genes can result in active protease.

By yet another method, mutations can be generated by allowing two dissimilar forms of subtilisin to undergo recombination in vivo. According to this method, homologous regions within the two genes lead to a cross-over of corresponding regions resulting in the exchange of genetic information. The generation of hybrid amylase molecules according to this technique is fully described in U.S. patent application Ser. No. 67,992, filed on Jun. 29, 1987, which is incorporated by reference in its entirety herein. An example of a plasmid which can generate hybrid forms of subtilisin is depicted in FIG. 5. Both the subtilisin 309 and 147 genes, incorporated into plasmid pSX143, are truncated, and therefore cannot themselves lead to subtilisin expression. However, if recombination occurs between the two genes so as to correct the defect produced by truncation, i.e., the N terminal region of the subtilisin 309 gene becomes linked to the C terminal region of the subtilisin 147 gene, then active, mutant subtilisin can be produced. If pSX143 is incorporated into a protease-negative strain of bacteria, and then bacteria who develop a protease positive phenotype are selected, then various mutants, subtilisin 309/147 chimeras, can be identified.

5.2.3. Generation of Site Directed Mutations in the Subtilisin Gene

Once the subtilisin gene has been cloned, and desirable sites for mutation identified, these mutations can be introduced using synthetic oligo nucleotides. These oligonucleotides contain nucleotide sequences flanking the desired mutation sites; mutant nucleotides are inserted during oligonucleotide synthesis. In a preferred method, a single stranded gap of DNA, bridging the subtilisin gene, is created in a vector bearing the subtilisin gene. Then the synthetic nucleotide, bearing the desired mutation, is annealed to a homologous portion of the single-stranded DNA. The remaining gap is then filled in by DNA polymerase I (Klenow fragment) and the construct is ligated using T4 ligase. A specific example of this method is described in Morinaga et al., (1984, Biotechnology 2:646–639). According to Morinaga et al., a fragment within the gene is removed using restriction endonuclease. The vector/gene, now containing a gap, is then denatured and hybridized to vector/gene which, instead of containing a gap, has been cleaved with another restriction endonuclease at a site outside the area involved in the gap. A single-stranded region of the gene is then available for hybridization with mutated oligonucleotides, the remaining gap is filled in by the Klenow fragment of DNA polymerase I, the insertions are ligated with T4 DNA ligase, and, after one cycle of replication, a double-stranded plasmid bearing the desired mutation is produced. The Morinaga method obviates the additional manipulation of construction new restriction sites, and therefore facilitates the generation of mutations at multiple sites. U.S. Pat. No. 4,760,025, by Estelle et al., issued Jul. 26, 1988, is able to introduce oligonucleotides bearing multiple mutations by performing minor alterations of the cassette, however, an even greater variety of mutations can be introduced at any one time by the Morinaga method, because a multitude of oligonucleotides, of various lengths, can be introduced.

5.3. Expression of Subtilisin Mutants

According to the invention, a mutated subtilisin gene produced by methods described above, or any alternative methods known in the art, can be expressed, in enzyme form, using an expression vector. An expression vector generally falls under the definition of a cloning vector, since an expression vector usually includes the components of a typical cloning vector, namely, an element that permits autonomous replication of the vector in a microorganism independent of the genome of the microorganism, and one or more phenotypic markers for selection purposes. An expression vector includes control sequences encoding a promoter, operator, ribosome binding site, translation initiation signal, and, optionally, a repressor gene. To permit the secretion of the expressed protein, nucleotides encoding a "signal sequence" may be inserted prior to the coding sequence of the gene. For expression under the direction of control sequences, a target gene to be treated according to the invention is operably linked to the control sequences in the proper reading frame. Promoter sequences that can be incorporated into plasmid vectors, and which can support the transcription of the mutant subtilisin gene, include but are not limited to the prokaryotic βlactamase promoter (Villa-Kamaroff, et al., 1978, Proc. Natl. Acad. Sci. U.S.A. 75:3727–3731) and the tac promoter (DeBoer, et al., 1983, Proc. Natl. Acad. Sci. U.S.A. 80:21–25). Further references can also be found in "Useful proteins from recombinant bacteria" in Scientific American, 1980, 242:74–94.

According to one embodiment B. subtilis is transformed by an expression vector carrying the mutated DNA. If expression is to take place in a secreting microorganism such as B. subtilis a signal sequence may follow the translation initiation signal and precede the DNA sequence of interest. The signal sequence acts to transport the expression product to the cell wall where it is cleaved from the product upon secretion. The term "control sequences" as defined above is intended to include a signal sequence, when it is present.

5.4. Screening of Mutant Subtilisins

For screening mutants, transformed B. subtilis can be cultivated in the presence of a filter material (such as nitrocellulose) to which the secreted expression product (e.g. enzyme) binds. In order to screen for an expression product having a desired characteristic, filter bound expression product is subjected to conditions which distinguish expression product of interest from wild-type expression product. For example, the filter-bound expression product can be subjected to conditions which would inactivate a wild-type product. Preserved enzyme activity following adverse treatment suggests that the mutation confers enhanced stability on the enzyme, and is therefore a useful mutation.

In one embodiment of the invention, screening for stable variants is accomplished using a protease deficient B. subtilis strain transformed with the variant plasmid and plated out as follows: a nitrocellulose filter is placed on a nutrient base in a petri dish, and a cellulose acetate filter is placed on top of the nitrocellulose. Colonies are grown on the cellulose acetate, and protease from individual colonies is secreted through the cellulose acetate onto the nitrocellulose filter where it is stably bound. Protease from hundreds of colonies is bound to a single filter allowing subsequent screening of thousands of different variants by processing multiple filters.

To identify colonies producing subtilisin of enhanced thermal stability, the filters can be incubated in buffer solutions at temperatures which would inactivate substantially all wild-type activity. Variants of enhanced stability or activity retain activity after this step. The suitably treated filter then is soaked in a solution containing Tosyl-L-Arg methyl ester (TAME) Benzoly-Arg-ethyl-ester (BAEE), Acetyl-Tyr-ethyl-ester (ATEE) (Sigma) or similar compounds. Because TAME, BAEE, and ATEE are substrates for the proteases they are cleaved in zones on the filter containing variant subtilisins which remain active after treatment. As cleavage occurs, protons are released in the reaction and cause phenol red to change in color from red to yellow in areas retaining protease activity.

This procedure can be used to screen for different classes of variants with only slight modifications. For example, the filters could be treated at high temperature, at high pH, with denaturants, oxidizing agents, or under other conditions which normally inactivate an enzyme such as a protease to find resistant variants. Variants with altered substrate specificity could be screened by replacing TAME, BAEE, or ATEE with other substrates which are normally not cleaved by wild-type subtilisin.

Once a variant of enhanced stability is identified by screening, the colony from which the variant is derived is isolated and the altered subtilisin is purified. Experiments can be performed on the purified enzyme to determine conditions of stability towards oxidation, thermal inactivation, denaturation temperature, kinetic parameters as well as other physical measurements. The altered gene can also be sequenced to determine the amino acid changes responsible for the enhanced stability. Using this procedure, variants with increased washing abilities have been isolated.

6. EXAMPLE

Site-Specific Mutation of the Subtilisin Gene Generates Mutants with Useful Chemical Characteristics

6.1. Materials and Methods 6.1.1. Bacterial Strains

B. subtilis 309 and 147 are variants of Bacillus lentus, deposited with the NCIB and accorded the accession numbers NCIB 10147 and NCIB 10309, and described in U.S. Pat. No. 3,723,250, issued Mar. 27, 1973, and incorporated in its entirety by reference herein. B. subtilis DN 497 is described in U.S. Ser. No. 039,298, also incorporated by reference herein, and is an aro$^+$ transformant of RUB 200 with chromosomal DNA from SL 438, a sporulation and protease deficient strain obtained from Dr. Kim Hardy of Biogen. E. coli MC 1000 r$^-$m$^+$ (Casa-daban, M. J. and Cohen, S. N. (1980), J. Mol. Biol. 138:179–207, was made r$^-$m$^+$ by conventional methods and is also described in U.S. Ser. No. 039,298.

Figure 3A:
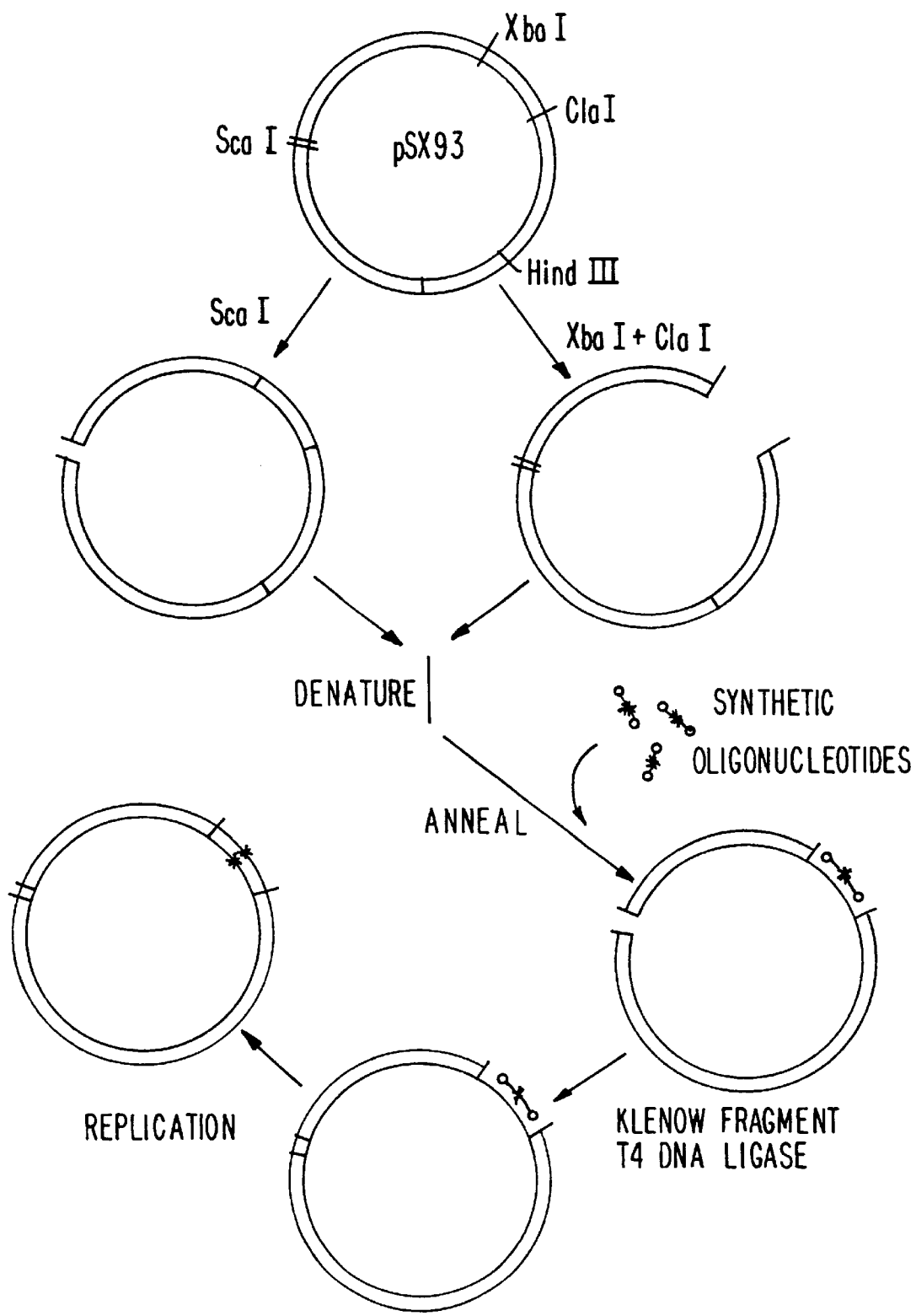

6.1.2. Plasmids pSX50 (described in U.S. patent application Ser. No. 039,298 filed Apr. 17, 1987, and incorporated by reference herein) is a derivative of plasmid pDN 1050, comprising the promoter-operator P$_1$O$_1$, the B. pumilus xyn B gene and the B. subtilis xyl R gene.

pSX65 (described in U.S. patent application Ser. No. 039,298, supra) is a derivative of plasmid pDN 1050, comprising the promotor-operator P$_2$O$_2$, the B. pumilus xyn B gene, and the B. subtilis xyl R gene.

pSX93, shown in FIG. 3a, is puC13 (Vieira and Messing, 1982, Gene 19:259–268) comprising a 0.7 kb XbaI-Hind III fragment of the subtilisin 309 gene including the terminator inserted in a polylinker sequence.

pSX119 is pUC13 harboring an EcoRI-XbaI fragment of the subtilisin 309 gene inserted into the polylinker.

pSX62 (described in U.S. patent application Ser. No. 039,298, supra) is a derivative of pSX52 (ibid), which comprises a fusion gene between the calf prochymosin gene and the B. pumilus xyn B gene inserted into pSX50 (supra). pSX62 was generated by inserting the E. coli rrn B terminator into pSX52 behind the prochymosin gene.

pSX92 was produced by cloning the subtilisin 309 into plasmid pSX62 (supra) cut at Cla I and Hind III and filled prior to the insertion of the fragments DraI-NheI and NheI-Hind III from the cloned subtilisin 309 gene.

6.1.3. Purification of Subtilisins

The procedure relates to a typical purification of a 10 liter scale fermentation of the Subtilisin 147 enzyme, the Subtilisin 309 enzyme or mutants thereof.

Approximately 8 liters of fermentation broth were centrifuged at 5000 rpm for 35 minutes in 1 liter beakers. The supernatants were adjusted to pH 6.5 using 10% acetic acid and filtered on Seitz Supra S100 filter plates.

The filtrates were concentrated to approximately 400 ml using an Amicon CH2A UF unit equipped with an Amicon S1Y10 UF cartridge. The UF concentrate was centrifuged and filtered prior to adsorption on a Bacitracin affinity column at pH 7. The protease was eluted from the Bacitracin column using 25% 2-propanol and 1 M sodium chloride in a buffer solution with 0.01 dimethylglutaric acid, 0.1 M boric acid and 0.002 M calcium chloride adjusted to pH 7.

The fractions with protease activity from the Bacitracin purification step were combined and applied to a 750 ml Sephadex G25 column (5 cm dia.) equilibrated with a buffer containing 0.01 dimethylglutaric acid, 0.2 M boric acid and 0.002 M calcium chloride adjusted to pH 6.5.

Fractions with proteolytic activity from the Sephadex G25 column were combined and applied to a 150 ml CM Sepharose CL 6B cation exchange column (5 cm dia.) equilibrated with a buffer containing 0.01 dimethylglutaric acid, 0.2 M boric acid and 0.002 M calcium chloride adjusted to pH 6.5.

The protease was eluted using a linear gradient of 0–0.1 M sodium chloride in 2 liters of the same buffer (0–0.2 M sodium chloride in case of sub 147).

In a final purification step protease containing fractions from the CM Sepharose column were combined and concentrated in an Amicon ultrafiltration cell equipped with a GR81P membrane (from the Danish Sugar Factories Inc.).

Subtillisin 309 and mutants
Met 222 to Ala
Gly 195 to Glu
Asn 218 to Ser
Arg 170 to Tyr
Gly 195 to Glu, Arg 170 to Tyr
Gly 195 to Glu, Met 222 to Ala
were purified by this procedure.

6.1.4. Oligonucledotide Synthesis

All mismatch primers were synthesized on an Applied Biosystems 380 A DNA synthesizer and purified by polyacrylamide gel electrophoresis (PAGE).

6.1.5. Determination of Oxidation Stability

The purified enzyme is diluted to an enzyme content of approximately 0.1 mg/ml in 0.01 M dimethylglutaric acid pH 7 and in the same buffer with 0.01 M peracetic acid (pH 7).

Both sets of dilutions were heated to 50° C. for 20 minutes. Proteolytic activity was measured in the dilutions before and after the heat treatment.

6.1.6. Assay for Proteolytic Activity

OPA-Casein Method

Proteolytic activity was determined using casein as the substrate. One Casein Protease Unit (CPU) is defined as the amount of enzyme liberating 1 millimole of primary amino groups (determined by comparison with a serine standard) per minute under standard conditions, i.e. incubation for 30 minutes at 25° C. and pH 9.5.

A 2% (w/v) solution of casein (Hammarstein, supplied by Merck A.G., West Germany) was prepared with the Universal Buffer described by Britton and Robinson (Journ.Chem.Soc. 1931, p. 1451), adjusted to pH 9.5.

Two ml of substrate solution was preincubated in a water bath for 10 minutes at 25° C. 1 ml of enzyme solution containing about 0.2–0.3 CPU/ml of Britton-Robinson buffer (pH 9.5), was added. After 30 minutes of incubation at 25° C. the reaction was terminated by the addition of a stopping agent (5 ml of a solution containing trichloroacetic acid (17.9 g), sodium acetate (29.9 g), and acetic acid (19.8 g), filled up to 500 ml with deionized water). A blank was prepared in the same manner as the test solution, except that the stopping agent was added prior to the enzyme solution.

The reaction mixtures were kept for 20 minutes in the water bath, whereupon they were filtered through Whatman° 42 paper filters.

Primary amino groups were determined by their colour development with o-phthaldialdehyde (OPA).

Disodium tetraborate decahydrate (7.62 g) and sodium dodecylsulfate (2.0 g) was dissolved in 150 ml of water. OPA (160 mg) dissolved in 4 ml of methanol was then added together with 400 μl of beta-mercaptoethanol, whereafter the solution was made up to 200 ml with water.

To the OPA reagent (3 ml) was added 40 μl of the above-mentioned filtrates with mixing. The optical density (OD) at 340 nm was measured after about 5 minutes.

The OPA test was also performed with a serine standard containing 10 mg of serine in 100 ml of Britton-Robinson buffer (pH 9.5). The buffer was used as a blank.

The protease activity was calculated from the optical density measurements by means of the following formula:

$$\text{CPU/ml of enzyme solution} = \frac{(OD_t - OD_b) \times C_{ser} \times Q}{(OD_{ser} - OD_B) \times MW_{ser} \times t_i}$$

$$\text{CPU/g of enzyme preparation} = \text{CPU/ml} \cdot b$$

wherein $OD_t$, $OD_b$, $OD_{ser}$ and $OD_B$ is the optical density of the test solution, blank, serine standard, and buffer, respectively, $C_{ser}$ the concentration of serine in mg/ml in the standard, $MW_{ser}$ the molecular weight of serine. Q is the dilution factor (in this instance equal to 8) for the enzyme solution, and ti is the incubation time in minutes.

In the following Table V, results from the above assay are shown relative to the parent enzyme.

6.1.7. Assay for Washability

Test cloths (7 cm×7 cm, approximately 1 g) were produced by passing desized cotton (100% cotton, DS 71) cloth through the vessel in a Mathis Washing and Drying Unit type TH (Werner Mathis AG, Zurich, Switzerland) containing spinach juice (produced from fresh spinach) and then through the pressure roll of the machine in order to remove excess spinach juice.

Finally the cloth was dried in a strong air stream at room temperature, stored at room temperature for 3 weeks, and subsequently kept at −18° C. prior to use.

The tests were performed in a Terg-O-tometer test washing machine (described in Jay C. Harris "Detergency Evaluation and Testing", Interscience Publishers Ltd., 1954, p. 60–61) isothermally for 10 minutes at 100 rpm. As detergent the following standard powder detergent was used:

| | | |
|---|---|---|
| LAS, Nansa S 80 | | 0.4 g/l |
| AE, Berol 0 65 | | 0.15 g/l |
| Soap | | 0.15 g/l |
| STPP | | 1.75 g/l |
| Sodium silicate | | 0.40 g/l |
| CMC | | 0.05 g/l |
| EDTA | | 0.01 g/l |
| Na$_s$SO$_4$ | | 2.10 g/l |
| Perborate | | 1.00 g/l |
| TAED | | 0.10 g/l |

TAED=N,N,N', N'-tetraacetyl-ethylene diamine; pH was adjusted with 4 N NAOH to 9.5. The water used was ca. 9•GH (German Hardness).

Tests were performed at enzyme concentrations of: 0, 0.05 CPU/1, and 0.1 CPU/1, and two independent sets of tests were performed for each of the mutants.

Eight cloths were used for each testing using one beaker (800 ml) of detergent. Of the cloths, four were clean and four were stained with spinach juice. Subsequent to the washing the cloths were flushed in running water for 25 minutes in a bucket.

The cloths were then air dried overnight (protected against day light) and the remission, R, determined on a ElREPHO 2000 spectrophotometer from Datacolor S.A., Dietkikon, Switzerland at 460 nm.

As a measure of the washing ability differential remission, ΔR, was used, Δ R being equal to the remission after wash with enzyme added minus the remission after wash with no enzyme added.

6.1.8. Assay for Thermostability

The same procedure as above for washability was used for estimating the thermostability of the mutants produced, by performing the test at temperatures of 40° C. and 60° C., respectively.

6.2. Results 6.2.1. Cloning of the Subtilisin 309 and 147 Genes

Chromosomal DNA from the "309" strain was isolated by treating a cell suspension with Lysozyme for 30 minutes at 37° C., and then with SDS for 5 minutes at 60° C. Subsequently, the suspension was extracted with phenol-chloroform (50:50), precipitated with ethanol, and the precipitate redissolved in TE. This solution was treated with RNase for 1 hour at 37° C.

Approximately 30 μg of the chromosomal DNA was partially digested with restriction enzyme Sau 3A (New England Biolabs) and fragments from about 1.5 kb to about 6.5 kb were isolated on DEAE cellulose paper from a 1% agarose gel (the subtilisin gene in other species is approximately 1.2 Kb in length).

As outlined in FIG. 1 the fragments were annealed and ligated to BamHI cut plasmid pSX50 (described in U.S. patent application Ser. No. 039,298 filed Apr. 17, 1987, which is hereby included for reference). The plasmids were then transformed into competent B. subtilis DN 497.

The cells were then spread on LB agar plates with 10 mM phosphate pH 7, 6 μg/ml chloramphenicol, and 0.2% xylose to induce the xyn-promoter in the plasmid. The plates also contained 1% skim milk so the protease producing transformants could be detected by the clear halo where the skim milk had been degraded.

Protease expressing clones were produced at a frequency of $10^{-4}$. Two clones were found that harboured plasmids carrying the gene for subtilisin 309, pSX86 and pSX88. The gene was then sequenced using the method of Maxam and Gilbert. The deduced nucleotide sequence of subtilisin 309 is presented in Table II.

TABLE II

THE SUBTILISIN 309 GENE

Signal

ATGAAGAAACCG TTGGGGAAAATT GTCGCAAGCACC GCACTACTCATT TCTGTTGCTTTT
1                         PRO
AGTTCATCGATC GCATCGGCTGCT GAAGAAGCAAAA GAAAAATATTTA ATTGGCTTTAAT
                        82
GAGCAGGAAGCT GTCAGTGAGTTT GTAGAACAAGTA GAGGCAAATGAC GAGGTCGCCATT

CTCTCTGAGGAA GAGGAAGTCGAA ATTGAATTGCTT CATGAATTTGAA ACGATTCCTGTT

TTATCCGTTGAG TTAAGCCCAGAA GATGTGGACGCG CTTGAACTCGAT CCAGCGATTTCT
                                                                Mature

TABLE II-continued
THE SUBTILISIN 309 GENE

Signal

```
TATATTGAAGAG GATGCAGAAGTA ACGACAATGGCG CAATCAGTGCCA TGGGGAATTAGC
                                      334
CGTGTGCAAGCC CCAGCTGCCCAT AACCGTGGATTG ACAGGTTCTGGT GTAAAAGTTGCT

GTCCTCGATACA GGTATTTCCACT CATCCAGACTTA AATATTCGTGGT GGCGCTAGCTTT

GTACCAGGGGAA CCATCCACTCAA GATGGGAATGGG CATGGCACGCAT GTGGCCGGGACG

ATTGCTGCTTTA AACAATTCGATT GGCGTTCTTGGC GTAGCGCCGAGC GCGGAACTATAC

GCTGTTAAAGTA TTAGGGGCGAGC GGTTCAGGTTCG GTCAGCTCGATT GCCCAAGGATTG

GAATGGGCAGGG AACAATGGCATG CACGTTGCTAAT TTGAGTTTAGGA AGCCCTTCGCCA
                                      XbaI
AGTGCCACACTT GAGCAAGCTGTT AATAGCGCGACT TCTAGAGGCGTT CTTGTTGTAGCG

GCATCTGGGAAT TCAGGTGCAGGC TCAATCAGCTAT CCGGCCCGTTAT GCGAACGCAATG

GCAGTCGGAGCT ACTGACCAAAAC AACAACCGCGCC AGCTTTTCACAG TATGGCGCAGGG

CTTGACATTGTC GCACCAGGTGTA AACGTGCAGAGC ACATACCCAGGT TCAACGTATGCC
                 ClaI
AGCTTAAACGGT ACATCGATGGCT ACTCCTCATGTT GCAGGTGCAGCA GCCCTTGTTAAA

CAAAAGAACCCA TCTTGGTCCAAT GTACAAATCCGC AATCATCTAAAG AATACGGCAACG

AGCTTAGGAAGC ACGAACTTGTAT GGAAGCGGACTT GTCAATGCAGAA GCGGCAACACGC
```

Stop
TAA

1141

Figure 2:
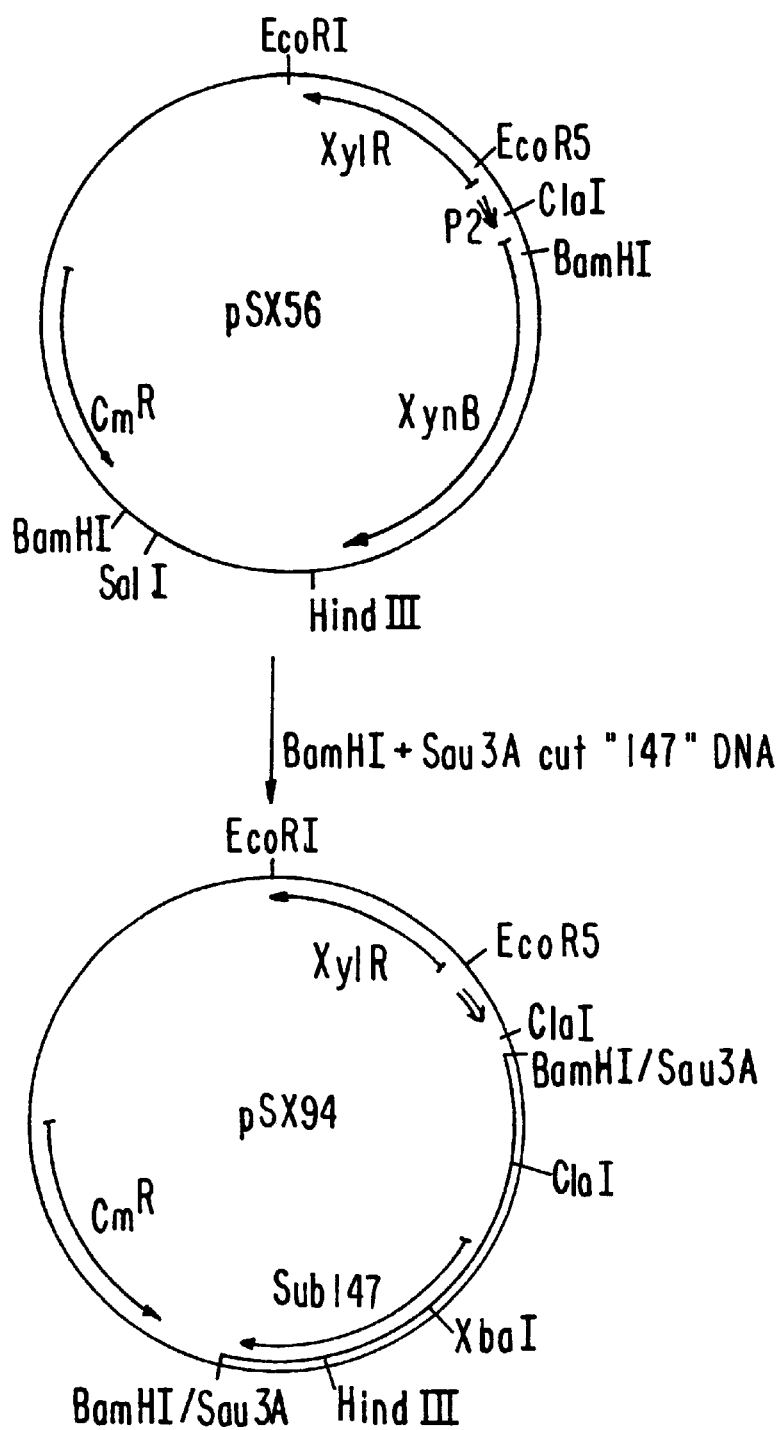

The same procedure as above was used for the cloning of the subtilisin 147 gene except that the DNA fragments were ligated into the plasmid pSX56 (also described in U.S. Ser. No. 039,298 supra), which as indicated in FIG. 2 instead of the xyn promotor harbours the xyl promotor. One clone was found harbouring a plasmid, pSX94, carrying the gene for subtilisin 147. The sequence for this gene is shown in table III below.

TABLE III
THE SUBTILISIN 147 GENE

Signal

```
ATGAGACAAAGT CTAAAAGTTATG GTTTTGTCAACA GTGGCATTGCTT TTCATGGCAAAC
1           Pro
CCAGCAGCAGCA GGCGGGGAGAAA AAGGAATATTTG ATTGTCGTCGAA CCTGAAGAAGTT
                73
TCTGCTCAGAGT GTCGAAGAAAGT TATGATGTGGAC GTCATCCATGAA TTTGAAGAGATT

CCAGTCATTCAT GCAGAACTAACT AAAAAAGAATTG AAAAAATTAAAG AAAGATCCGAAC
                                                            Mature
GTAAAAGCCATC GAAGAGAATGCA GAAGTAACCATC AGTCAAACGGTT CCTTGGGGAATT
                                               280
TCATTCATTAAT ACGCAGCAAGCG CACAACCGCGGT ATTTTTGGTAAC GGTGCTCGAGTC

GCTGTCCTTGAT ACAGGAATTGCT TCACACCCAGAC TTACGAATTGCA GGGGGAGCGAGC

TTTATTTCAAGC GAGCCTTCCTAT CATGACAATAAC GGACACGGAACT CACGTGGCTGGT

ACAATCGCTGCG TTAAACAATTCA ATCGGTGTGCTT GGTGTACGACCA TCGGCTGACTTG

TACGCTCTCAAA GTTCTTGATCGG AATGGAAGTGGT TCGCTTGCTTCT GTAGCTCAAGGA

ATCGAATGGGCA ATTAACAACAAC ATGCACATTATT AATATGAGCCTT GGAAGCACGAGT

GGTTCTAGCACG TTAGAGTTAGCT GTCAACCGAGCA AACAATGCTGGT ATTCTCTTAGTA

GGGGCAGCAGGT AATACGGGTAGA CAAGGAGTTAAC TATCCTGCTAGA TACTCTGGTGTT

ATGGCGGTTGCA GCAGTTGATCAA AATGGTCAACGC GCAAGCTTCTCT ACGTATGCCCA
```

TABLE III-continued

THE SUBTILISIN 147 GENE

Signal

GAAATTGAAATT TCTGCACCTGGT GTCAACGTAAAC AGCACGTACACA GGCAATCGTTAC

GTATCGCTTTCT GGAACATCTATG GCAACACCACAC GTTGCTGGAGTT GCTGCACTTGTG

AAGAGCAGATAT CCTAGCTATACG AACAACCAAATT CGCCAGCGTATT AATCAAACAGCA

ACGTATCTAGGT TCTCCTAGCCTT TATGGCAATGGA TTAGTACATGCT GGACGTGCAACA

Stop

CAATAA

1084

6.2.2. Generation of Site-Specific Mutations of the Subtilisin 309 Gene

Site specific mutations were performed by the method of Morinaga et al. (Biotechnology, supra). The following oligonucleotides were used for introducing the mutations:

a) Gly-195 Glu:

A 27-mer mismatch primer, Nor-237, which also generates a novel SacI restriction site

```
        5' CACAGTATGGGCGCAGGGCTTGACATTGTCGCACCAGG 3'
NOR-    5' GTATGGCGCAGAGCTCGACATTTGTCGC 3'
237                    SacI
``` b) Gly-195 Asp:

A 23-mer mismatch primer, NOR-323, which also generates a novel BglII site

```
                 AT
5' CACAGTATGGGCGCAGGGCTTGACATTGTC 3'
   3' CATACCGCGTCTAGAACTGTAAC    5'
              BglII
``` c) Met-222 Cys:

A 24-mer mismatch primer, NOR-236

```
                    ClaI
          5' AGCTTAAACGGTACATCGATGGCTACTCCTCATGTT 3'
NOR-236   5' ACGGTACATCGTGCGCTACTCCTC 3'
``` d) Met-222 Ala:

A 22-mer mismatch primer, NOR-235

```
                    ClaI
          5' AGCTTAAACGGTACATCGATGGCTACTCCTCATGTT 3'
NOR-235       5' CGGTACATCGGCGGCTACTCCT 3'
```

Both of these primers destroy the unique ClaI site e) Ser-153 Ala:

An 18-mer mismatch primer, NOR-324, which also generates a novel PvuII site

```
                                G
          5' CTTGTAGCGGCATCTGGGAATTCAGGT 3'
NOR-324   3' CATCGCCGTCGACCCTTA 5'
                    PvuII
``` f) Asn-218 Ser:

A 23-mer mismatch primer, NOR-325, which also generates a novel MspI site

```
                        TC
          5' TATGCCAGCTTAAACGGTACATCGATG 3'
NOR-324   3' TACGGTCGAATAGGCCATGTAGC 5'
                         MspI
``` g) Thr-71 Asp:

A 23-mer mismatch primer, NOR-483,

```
                        GAC
          5' TGTGGCCCGGGACGATTGCTGCTT 3'
NOR-483   3' ACACCGGCCCCCTGTAACGACGAA 5'
``` h) Met-222 Cys and Gly-219 Cys:

A 32-mer mismatch, NOR-484,

```
                T        TGT
          5' CAGCTTAAACGGTACATCGATGGCTACTCCTC 3'
                       219     222
NOR-484   3' GTCGAATTTGACATGTAGCACACGATGAGGAG 5'
``` i+j) Gly-195 Glu and Met-222 Ala or Met-222 Cys:

For these double mutants combinations of NOR-237 and NOR-235 or NOR-236 were performed by joining the single mutant DNA-fragments.

k) Ser-153 Ala and Asn-218 Ser:

A combination of NOR-324 and NOR-325 was performed in analogy with the above.

Figure 3B:
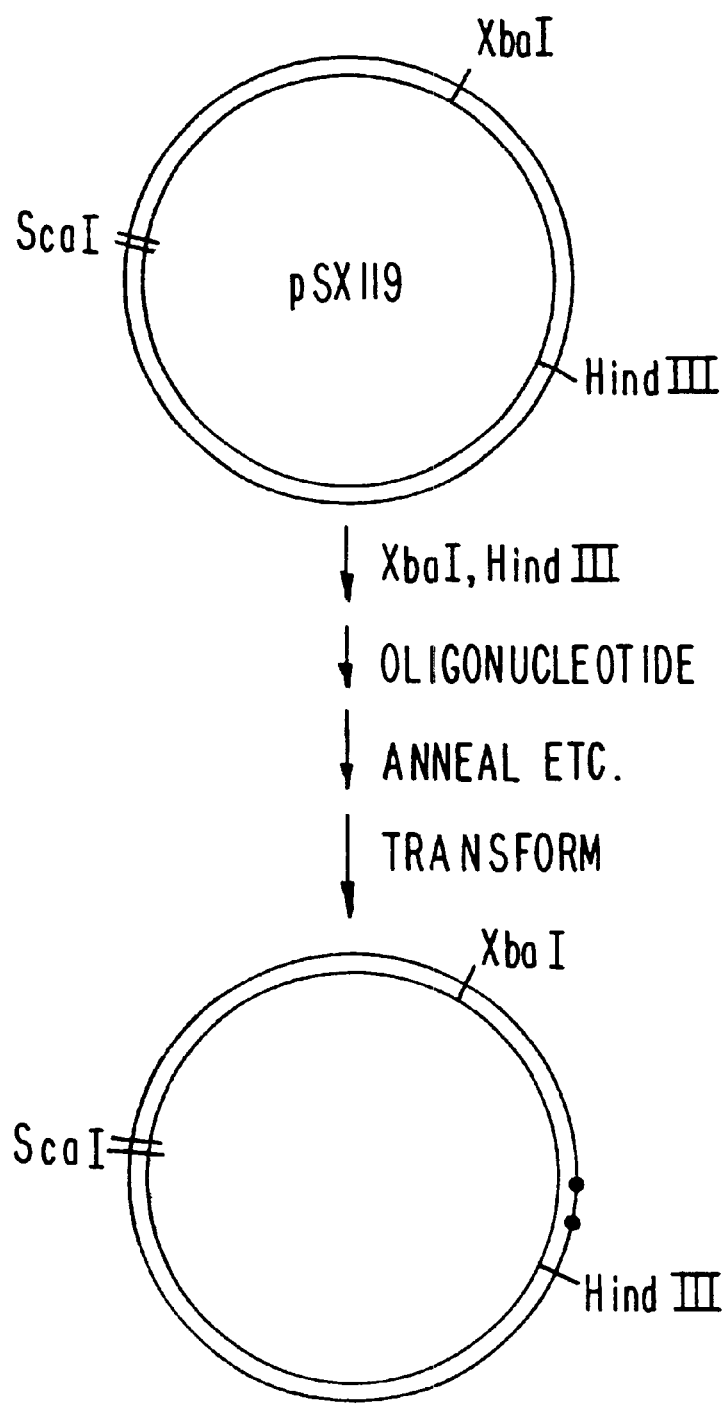

Gapped duplex mutagenesis was performed using the plasmid pSX93 as template. pSX93 is shown in FIG. 3a and 3b, and is pUC13 (Vieira, J. and Messing, J.: 1982, Gene 19: 259–268) harbouring an 0.7 kb XbaI-HindIII fragment of the subtilisin 309 gene including the terminator inserted in the polylinker. The terminator and the HindIII site are not shown in Table II.

For the introduction of mutations in the N-terminal part of the enzyme the plasmid pSX119 was used. pSX119 is pUC13 harbouring an EcoRI-XbaI fragment of the subtilisin 309 gene inserted into the polylinker. The templates pSX93 and pSX119 thus cover the whole of the subtilisin 309 gene.

The mutations a), b), and e) were performed by cutting pSX93 with XbaI and ClaI as indicated in FIG. 3a; c), d), f), and h) were performed by cutting pSX93 with XbaI and HindIII as indicated in FIG. 3b.

Mutation g) was performed correspondingly in pSX119 by cutting with EcoRI and XbaI.

The double mutants i) and j) were produced by cutting the 0.7 kb Xba-HindIII fragment from a) partially with HgiAI (HgiAI also cuts in SacI, which was introduced by the mutation). This 180 bp XbaI-HgiAI fragment and the 0.5 kb HgiAI fragment from the c) and d) mutants, respectively, were ligated to the large HindIII-XbaI fragment from pSX93.

The double mutant k) was produced as above by combining mutants e) and f).

Subsequent to annealing, filling and ligation the mixture was used to transform *E. coli* MC 1000 r⁻m⁺. Mutants among the transformants were screened for by colony hybridization as described in Vlasuk et al.: 1983, J. Biol. Chem., 258: 7141–7148 and in Vlasuk, G.P. and Inouye, S.: p. 292–303 in "Experimental Manipulation of Gene Expression" Inouye, M. (ed.) Academic Press, New York. The mutations were confirmed by DNA sequencing.

6.2.3. Expression of Mutant Subtilisins

Subsequent to sequence confirmation of the correct mutation the mutated DNA fragments were inserted into plasmid pSX92, which was used for producing the mutants.

Figure 4:
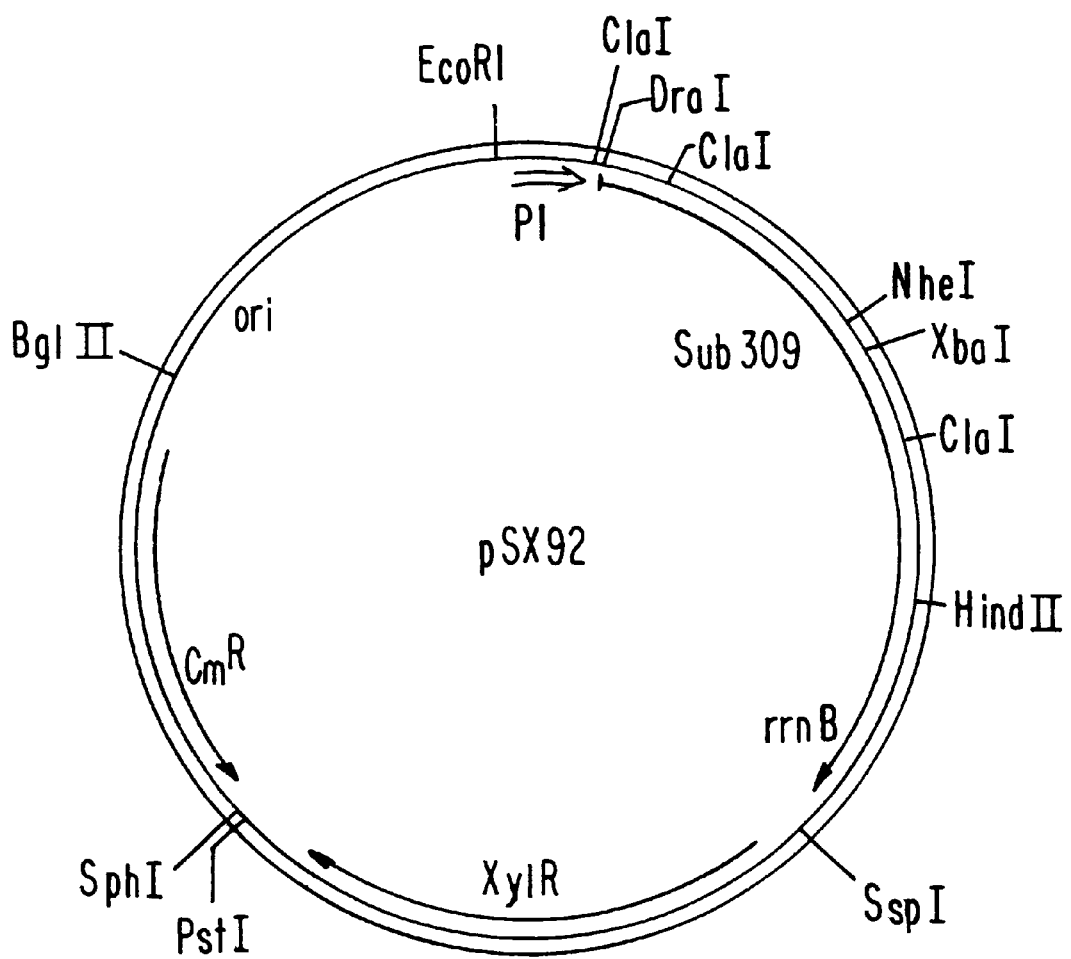
FIG. 4 illustrates plasmid pSX92, which is a derivative of plasmid pSX62, bearing the subtilisin 309 gene. Mutated fragments (i.e., XbaI-ClaI, XbaI-HindIII, or Eco RI-XbaI), excised from mutation plasmid pSX93 or pSX119 (see FIG. 3) using the appropriate restriction endonucleases, were inserted into plasmid pSX92 for expression in B. subtilis strain DN 497.

Plasmid pSX92 is shown in FIG. 4 and was produced by cloning the Sub 309 gene into plasmid pSX62 cut at ClaI, filled in with the Klenow fragment of DNA polymerase I, and cut with HindIII prior to the insertion of the fragments DraI-NheI and NheI-HindIII from the cloned Sub 309 gene.

To express the mutants the mutated fragments (XbaI-ClaI, XbaI-HindIII, or EcoRI-XbaI) were excised from the appropriate mutation plasmid pSX93 or pSX119, respectively, and inserted into pSX92.

The mutated pSX92 was then used to transform B. subtilis strain DN497, which was then grown in the same medium and under the same conditions as used for the cloning of the parent gene.

After appropriate growth the mutated enzymes were recovered and purified.

6.2.4. Oxidation Stability of Mutant Subtilisins

The mutants a) and d) were tested for their oxidation stability in 0.01 M peracetic acid after 20 minutes at 50° C. and pH 7. The parent strain NCIB 10309 protease was used as reference.

The results are indicated in Table IV below, which presents the residual proteolytic activity in the heat treated samples relative to samples untreated by oxidant or heat.

TABLE IV

Oxidation Stability Towards Peracetic Acid

| Enzyme | Residual Activity after 20 min. at 50° C. | |
| --- | --- | --- |
| | without oxidant | with oxidant |
| sub 309 | 89% | 48% |
| mutant a | 83% | 45% |
| mutant d | 92% | 93% |

It is concluded that mutant d (Met 222 to Ala) exhibits superior oxidation stability realtive to the parent enzyme and mutant a.

All the mutants except g) and h) have also been tested qualitatively in 100–500 ppm hypochlorite at room temperature and 35° C., pH 6.5 and 9.0, for from 15 minutes to 2 hours.

These tests showed that mutants c), d), i), and j) (all Met-222) could resist 3–5 times more hypochlorite than the other mutants.

When tested in a liquid detergent of the usual built type it was found that mutant f) exhibited superior stability compared to both the other mutants and the "parent" enzyme.

6.2.5. Proteolytic Activity of Mutant Subtilisins

The proteolytic activity of various mutants was tested against casein as protein substrate, according to methods detailed supra. The results are presented in Table V.

From the table it is seen that mutant a) exhibits enhanced activity compared to the parent. It is also seen that the Met-222 mutants have lower activity than the parent, but due to their improved oxidation stability their application in detergent compositions containing oxidants is not precluded.

TABLE V

Proteolytic Activity of Mutant Subtilisins

| Mutant | Relative Activity |
| --- | --- |
| None | 100 |
| a) | 120 |
| b) | 100 |
| c) | 30 |
| d) | 20 |
| e) | 100 |
| f) | 100 |
| i) | 20 |
| j) | 30 |

6.2.6. Washability of Mutant Subtilisins

The washability of various mutants was tested against spinach juice according to methods detailed supra. The results are presented in Table VI.

From the table it is seen that all of the tested mutants exhibited an improved washing ability compared to the parent enzyme, and that mutants c), d), i), and j) are markedly superior.

TABLE VI

Washing Ability of Mutant

| Mutant | $\overline{\Delta R}$ Concentration | (CPU/l) |
| --- | --- | --- |
| | 0.05 | 0.1 |
| none | 14.4 | 20.4 |
| a) | 18.8 | 21.5 |
| b) | 16.9 | 19.7 |
| c) | 21.8 | 23.8 |
| d) | 22.2 | 23.4 |
| e) | 15.4 | 21.8 |
| f) | 16.6 | 19.3 |
| i) | 21.6 | 22.1 |
| j) | 20.6 | 22.6 |

95% confidence interval: ±0.9

6.2.7. Thermostability of Mutant Subtilisins

The thermostability of mutant f) was tested against the wild type enzyme by using the washability test at 40° C. and 60° C., respectively. The results are shown in Table VII.

From the table it is seen that mutant f) at 60° C. shows a much improved washability compared to the wild type enzyme, whereas at 40° C. the washability of mutant f) is only slightly better than wild type enzyme.

TABLE VII

Washability at Different Temperatures

| Mutant | $\overline{\text{AR}}$ Concentration | (CPU/l) |
|---|---|---|
|  | 0.05 | 0.1 |
| none (40° C.) | 14.4 | 20.4 |
| f) (40° C.) | 16.6 | 19.3 |
| none (60° C.) | 15.1 | 24.9 |
| f) (60° C.) | 30.4 | 31.3 |

95% confidence interval ±0.9 (40° C.) and ±0.7 (60°)

6.3. Discussion

Subtilisin genes were cloned from the 147 and 309 variants of the bacterium *Bacillus lentus*, and the cloned genes were sequenced. By comparing the deduced amino acid sequences of subtilisins 147 and 309 one with the other and with sequences of other subtilisins, sites which, upon mutation, might alter the physical properties of the parent enzyme were identified. Site-directed mutagenesis was used to generate mutations at several of these sites in the subtilisin 309 gene. The resulting mutant enzymes were then expressed in a Bacillus strain, and tested against various physical and chemical parameters. Several of the mutants were shown to have improved stability to oxidation, increased proteolytic ability, or improved washability when compared with parent subtilisin 309 enzyme. These mutants exhibit properties desirable in enzymes comprised in detergent compositions.

What is claimed is:

1. A modified subtilisin 309, comprising one or more of the following mutations:
   (a) a substitution of the amino acid at position 153 with alanine;
   (b) a substitution of the amino acid at position 170 with tyrosine; and
   (c) a substitution of the amino acid at position 219 with methionine or cysteine; wherein each position corresponds to the position of the amino acid sequence of the mature subtilisin BPN' as depicted in Table I and the modified subtilisin has augmented protease activity or improved washing ability.

2. The modified subtilisin of claim 1, comprising a substitution of the amino acid at position 153 with alanine.

3. The modified subtilisin of claim 2, further comprising a substitution of the amino acid at position 218 with serine.

4. The modified subtilisin of claim 1, comprising a substitution of the amino acid at ion 170 with tyrosine.

5. The modified subtilisin of claim 1, comprising a substitution of the amino acid at ion 219 with methionine.

6. The modified subtilisin of claim 1, comprising a substitution of the amino acid at ion 219 with cysteine.

7. The modified subtilisin of claim 6, further comprising a substitution of the amino acid at position 222.

8. The modified subtilisin of claim 7, wherein the substitution of the amino acid at position 222 is with serine.

9. A detergent composition comprising a modified subtilisin of claim 1 and a surfactant.

* * * * *